United States Patent
Benatti

(12) 
(10) Patent No.: US 6,610,024 B1
(45) Date of Patent: Aug. 26, 2003

(54) MULTIPURPOSE MACHINE FOR MONITORING AND CONTROL OF LOCOREGIONAL THERAPIES IN ONCOLOGY

(76) Inventor: Luigi Benatti, 41037 Mirandola, Via Felice Cavallotti, 32 (IT)

( * ) Notice: Subject to any disclaimer, the term of this patent is extended or adjusted under 35 U.S.C. 154(b) by 0 days.

(21) Appl. No.: 09/481,443

(22) Filed: Jan. 14, 2000

(30) Foreign Application Priority Data

Nov. 16, 1999 (IT) ........................................ MO99A0259

(51) Int. Cl.[7] .......................... A61M 37/00; A61N 1/30
(52) U.S. Cl. ........................ 604/4.01; 604/6.09; 604/19
(58) Field of Search .............................. 604/4.01, 5.01, 604/5.04, 6.07, 6.09, 6.1, 6.11, 6.13, 19, 27, 29, 30, 31, 65–67, 80–83, 890.1; 424/140.1, 145.1, 529; 210/645–646, 739, 741, 198.1

(56) References Cited

U.S. PATENT DOCUMENTS

| | | | | |
|---|---|---|---|---|
| 4,192,302 A | * | 3/1980 | Boddie ................... | 128/DIG. 3 |
| 5,069,662 A | * | 12/1991 | Bodden .................. | 604/101.05 |
| 5,209,717 A | * | 5/1993 | Schmoll et al. ............ | 604/5.01 |
| 5,277,820 A | * | 1/1994 | Ash ........................... | 210/117 |
| 5,494,822 A | * | 2/1996 | Sadri ........................... | 417/22 |
| 5,722,947 A | * | 3/1998 | Jeppsson et al. ..... | 128/DIG. 12 |
| 5,910,252 A | * | 6/1999 | Truitt et al. ................. | 210/103 |

* cited by examiner

Primary Examiner—Angela D. Sykes
Assistant Examiner—Leslie R. Deak
(74) Attorney, Agent, or Firm—Wolf Greenfield & Sacks, P.C.

(57) ABSTRACT

The multipurpose machine for monitoring and control of locoregional therapies in oncology comprises a head which has a box-like structure, is supported by a stand provided with means for modifying its dimensions, and is provided with adsorbent and/or filtering means and with means for controlling and regulating chemotherapy and chemofiltration which are arranged along a first set of duct circuits accommodated in the head; the first set of circuits is divided into at least two loops, each of which has its own pumping means; the loops are mutually interactive or separable, and the first loop is provided for the infusion of the chemotherapeutic agents and the second loop is provided for the filtration of the chemotherapeutic agents; an emergency electronic circuit is inserted between the two loops in order to detect malfunctions of the pumping means and functionally restore at least the infusion loop; the head furthermore accommodates a second main set of circuits which can be activated alternately with respect to the first one and is meant to perform intraperitoneal hyperthermal perfusion therapy.

26 Claims, 4 Drawing Sheets

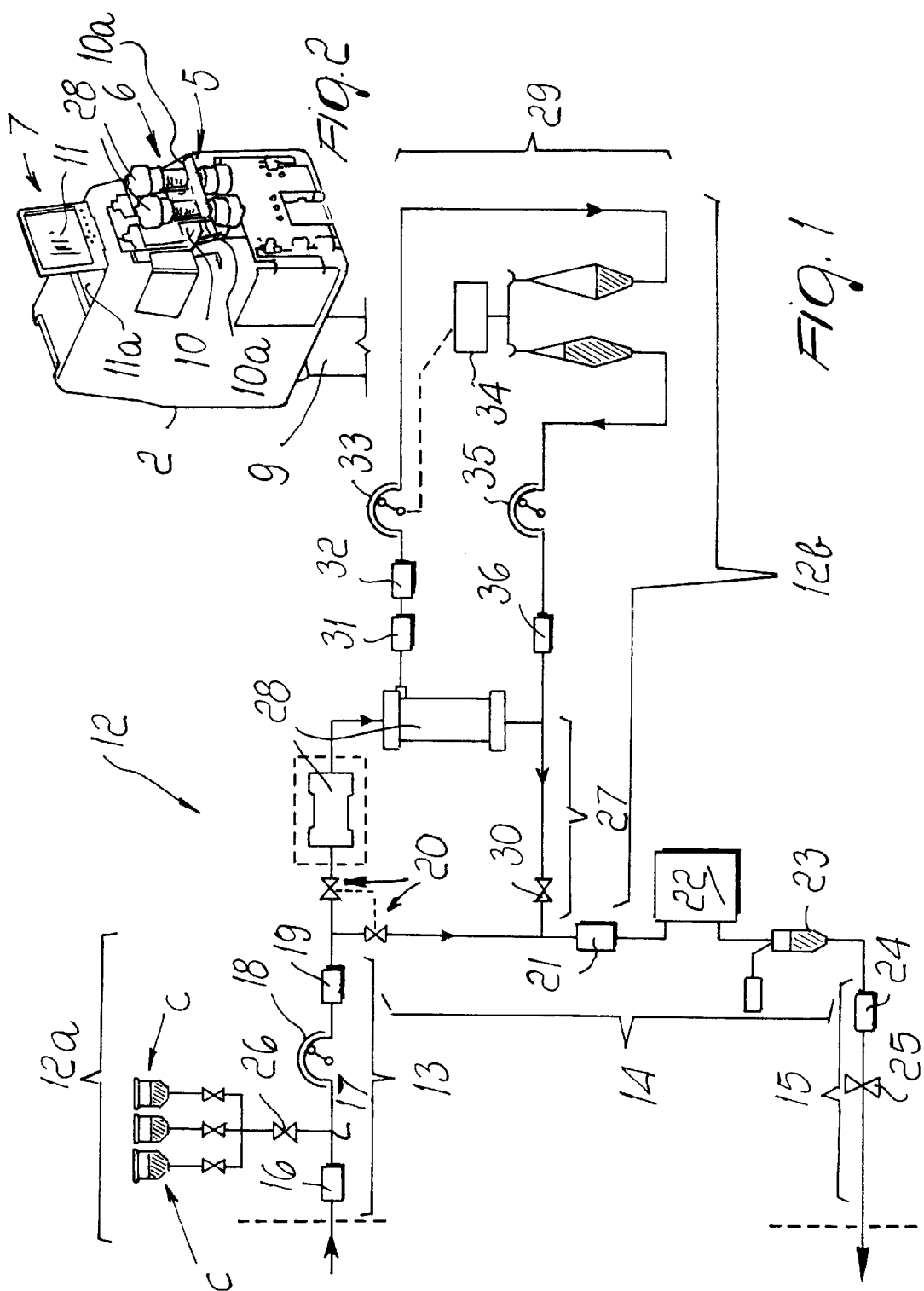

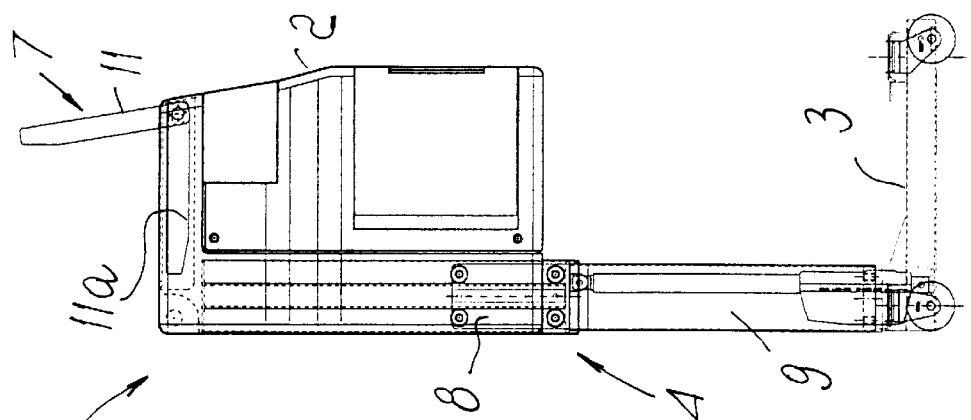
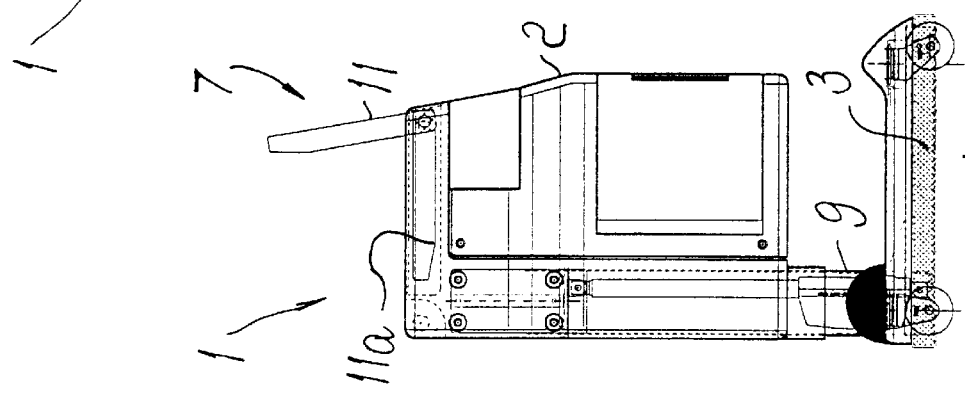
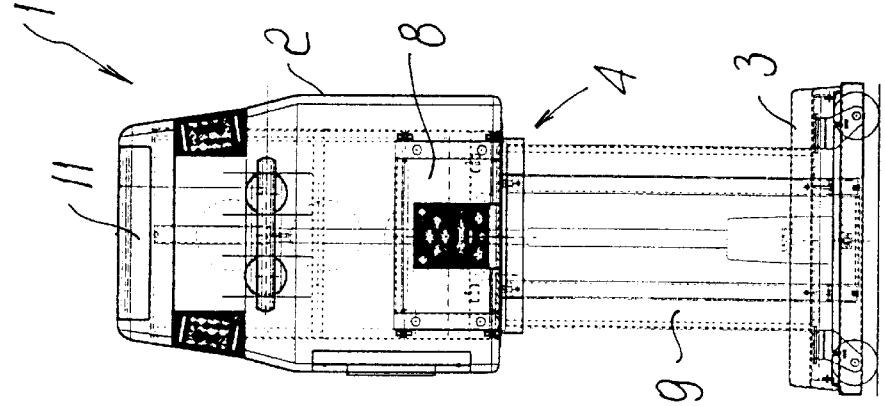
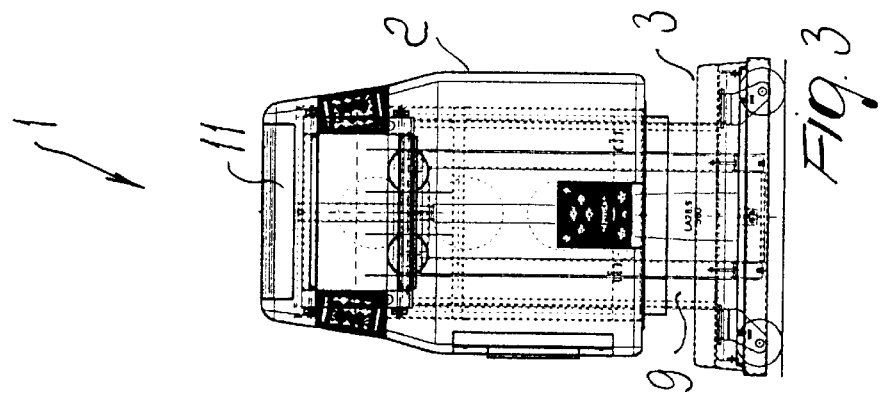

MULTIPURPOSE MACHINE FOR MONITORING AND CONTROL OF LOCOREGIONAL THERAPIES IN ONCOLOGY

This application claims priority to Italian Application Ser. No. MO99A000259 filed Nov. 16, 1999, the disclosure of which is incorporated herein by reference. The disclosure of Italian Application Ser. No. MO98A000162 is also incorporated herein by reference.

BACKGROUND OF THE INVENTION

The present invention relates to a multipurpose machine for monitoring and control of locoregional therapies in oncology.

Locoregional therapies currently applied in oncology use techniques which provide for the surgical or radiological insertion of special vascular catheters with two or three passages, in order to reach and directly perfuse the tumor or the body region invaded by the neoplasia.

It has in fact been demonstrated that the locoregional administration of antiblastic medicines leads to increased local concentration thereof, with exposure of the carcinogenic cells to more effective pharmacological levels.

In particular, perfusion methods have been recently developed which provide for simultaneous arterial and venous blockage and allow to artificially create localized metabolic situations such as hypoxia, hyperoxia or hyperthermia, all of which are harmful for the tumor and instead extremely useful for boosting the effectiveness of the antineoplastic medicines used.

The best-known and most widely used techniques are the hypoxic perfusion (so-called stop-flow) with subsequent filtration, and the intraperitoneal hyperthermal chemoperfusion (known as IPHC).

Hypoxic perfusion requires, throughout its execution, constant and attentive monitoring and control of the parameters during its main steps, which can be summarized as follows:

perfusion of the organ, after isolating it, with a flow of medicine which can vary between 80 and 120 ml/min according to the systemic pressure of the patient;

infusion of the chemotherapeutic agents according to predefined patterns, sequences and timings, but most of all according to the state of oxygenation of the tissues or of the blood in locoregional circulation;

time-controlled circulation of the chemotherapeutic agent;

filtration of the chemotherapeutic agent in locoregional circulation by using the hemofiltration and/or hemodialysis technique;

filtration of the chemotherapeutic agent in systemic circulation by means of the hemofiltration or hemodialysis technique, with associated control of the fluid balance of the patient.

Intraperitoneal hyperthermal perfusion instead consists in perfusing the peritoneal cavity with a solution which contains chemotherapeutic medicines at a controlled temperature of 42.5° C.

Both the flow of the solution and the duration of the perfusion are established according to preset patterns.

Hyperthermal perfusion can be performed with the abdomen open or closed, after inserting and adequately placing heat sensors, usually at least five, in the intraperitoneal cavity and four catheters which are connected to the perfusion/circulation circuit, in which the flow is controlled by means of a pump of the peristaltic type.

Execution of these therapies has always been entrusted exclusively to the professional experience of physicians and health workers, who have used devices assembled in a makeshift fashion and under their direct responsibility. A further risk exists of forced interruption of the therapy due to interruptions in the public electric main powering these devices at a moment when the chemotherapeutic agents are already perfused into the patient's body at their highest concentration and they cannot be removed any more, which seriously threatens the safety of the patient.

Moreover, in the current state of the art there is no device which allows to perform the above-described intraperitoneal hyperthermal therapy.

Furthermore, conventional devices used by medical staff rely on the constancy of the delivery of mains electric power for their operation.

SUMMARY OF THE INVENTION

The aim of the present invention is to solve the above-described problems of the prior art by providing a multipurpose machine for monitoring and control of locoregional therapies in oncology which allows medical and paramedic staff to perform both hypoxic perfusion and intraperitoneal hyperthermal perfusion therapies with a fully automated procedure and with maximum safety for the patient, with constant control of every physiological parameter involved and which further allows, if necessary, any direct corrective action by medical and paramedic staff.

An object of the present invention is to provide medical and paramedical staff with a multipurpose machine for monitoring and control of locoregional therapies in oncology which has an extremely compact structure, is easy to carry and absolutely reliable in operation even in case of an interruption of the mains electric power supply or in case of technical failure of the pumping means employed, particularly the main one located along the first loop.

This aim, this object and others are all achieved by a multipurpose is machine for monitoring and control of locoregional therapies in oncology, characterized in that it is constituted by a head which has a box-like structure and is supported by a stand which has means for modifying its dimensions, this head being in turn provided with elements for supporting packages of adsorbent means and/or for regulating chemotherapy and chemofiltration.

Conveniently, the multipurpose machine for monitoring and control of locoregional therapies in oncology is characterized in that the head accommodates a first set of duct circuits which forms at least two interactive or separable main loops, a first one for infusing the chemotherapeutic agents and a second one for filtering the chemotherapeutic agents.

Advantageously, the multipurpose machine is also characterized in that the head accommodates a second set of duct circuits which can be activated as an alternative to the first set of duct circuits in order to perform intraperitoneal hyperthermal perfusion therapy.

BRIEF DESCRIPTION OF THE DRAWINGS

Further characteristics and advantages will become apparent from the following description of a preferred embodiment of a multipurpose machine for monitoring and control of locoregional therapies in oncology, illustrated only by way of non-limitative example in the accompanying drawings, wherein:

FIG. 1 is a schematic view of a simplified version of the multipurpose machine, provided with a single functional set of circuits for monitoring and control of locoregional chemotherapy and chemofiltration;

FIG. 2 is a reduced-scale view of a head which is part of the machine according to the invention, in the simplified version of FIG. 1;

FIG. 3 is a front view of the machine according to the invention in the compact configuration for carrying;

FIG. 4 is a corresponding front view of the machine in the configuration for use;

FIG. 5 is a corresponding side view of FIG. 3;

FIG. 6 is a corresponding side view of FIG. 4;

DESCRIPTION OF THE PREFERRED EMBODIMENTS

Figure 7:
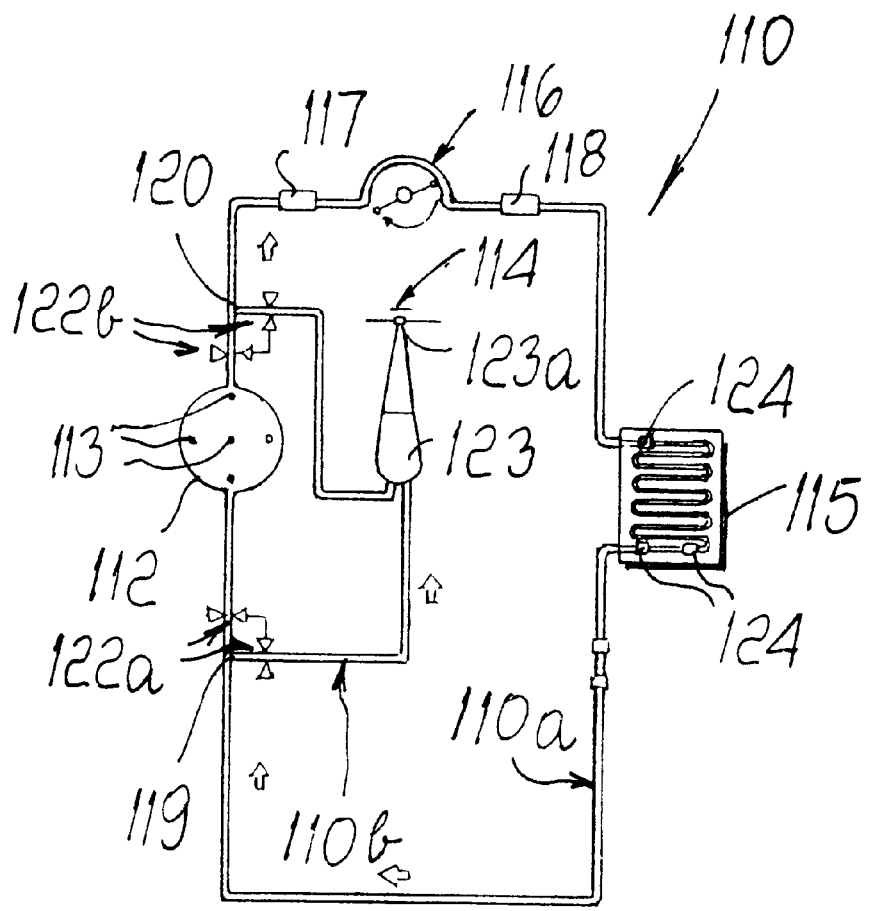
FIG. 7 is a diagram of a second set of duct circuits for performing intraperitoneal hyperthermal locoregional chemotherapy which can be inserted in the head of the multipurpose machine according to the invention in the more complete version thereof.

With reference to the above-mentioned figures, 1 designates a multipurpose machine for monitoring and control of locoregional therapies in oncology, comprising a head 2 which has a box-like structure and is supported by a base 3 provided with means 4 for modifying the overall dimensions of the machine 1.

The head 2 is also provided with elements 5 for supporting adsorbent and/or filtering means, generally designated by 6, and with means 7 for controlling and regulating chemotherapy and chemofiltration.

These dimension-modifying means 4 are constituted by a trolley 8 which is integrated in the head 2 and is slidingly guided on a vertical post 9 which rises from the base 3.

In turn, the supporting elements 5 are constituted by at least one plate 10 mounted so as to fold away in the front part of the head 2 and provided with corresponding recesses 10a for accommodating and retaining the packages 6.

The control and regulation means 7 are constituted by a controller, which is provided with a touch-screen monitor 11 arranged at the top of the head 2; the monitor also can be folded back onto the head into a fold-away position in a provided hollow seat 11a.

In a possible simplified version of the machine 1, the head 2 accommodates a set of duct circuits 12 forming at least two interactive or separable loops, a first one 12a for the infusion of chemotherapeutic agents and a second one 12b for the filtration of the chemotherapeutic agents.

In turn, the first loop 12a can be further divided ideally into at least three mutually sequential duct segments: a first segment 13 for drawing blood from the patient and for introducing the chemotherapeutic agents; a second intermediate segment 14 for blood control; and a third segment 15 for returning the blood to the patient.

The first segment 13 is provided, in a cascade arrangement, with a first sensor means 16 for sensing the patient's withdrawal blood pressure. The sensor means is connected to a point for introducing the chemotherapeutic agents, designated by 17, downstream of which there is a peristaltic pump 18 which constitutes the pumping assembly and is in turn followed by a second sensor 19 for controlling the inlet pressure of the second loop 12b for filtration of the chemotherapeutic agents.

The intermediate segment 14 is provided, again in a series arrangement, with a first valve means 20 for throttling or connecting the first loop 12a to the second loop 12b ; the valve means 20 is connected to a means 21 for sensing the oxygen pressure in the blood that flows in the first loop 12a, and downstream of the means there is a heating means 22 connected to a third sensor 23 for measuring pressure of the blood returning to the patient.

The third segment 15 for return to the patient is provided, in a series arrangement, with a fourth sensor 24 for detecting any air present in the blood returned to the patient and at least one terminal electric clamp 25 to prevent reverse flow of the blood.

The point 17 where the chemotherapeutic agents are introduced is controlled with a valve means 26 of the multiple-way type which can be driven both sequentially and on a time-controlled basis.

In one possible embodiment, the oxygen pressure sensor 21 is constituted by a conventional sound or probe of the invasive type which is adapted to be placed in direct contact with an organ which is the target of chemotherapeutic agents.

The second loop 12b for filtering the chemotherapeutic agents also is ideally composed of two sub-loops: a first sub-loop 27, provided with at least one chemotherapeutic agent adsorbent and/or filtering means 28, and a second sub-loop 29 for controlling fluid circulation, controlling the integrity of the filtering means 28 and maintaining a presettable water balance of the patient.

The first sub-loop 27 can be connected in input to the intermediate segment 14 of the first loop 12a through the throttling and/or connection valve means 20 and in output directly upstream of the blood oxygen pressure sensor means 21; before the output connection, in the sub-loop 27 there is at least one electric clamp 30 for throttling the connection.

The second sub-loop 29 is essentially constituted by a conventional circuit for hemofiltration or hemodialysis and is provided with at least one fifth sensor means 31 for detecting any blood presence inside the second sub-loop 29.

Downstream of the fifth sensor means 31 there is a sixth sensor means 32 for detecting the pressure in output from the filtering means, downstream of which there is a second pumping assembly 33 followed by a weighing station 34 and by a third pumping assembly 35, downstream of which there is a seventh sensor means 36 for detecting and controlling the pressure in the second sub-loop 29.

Figure 8:
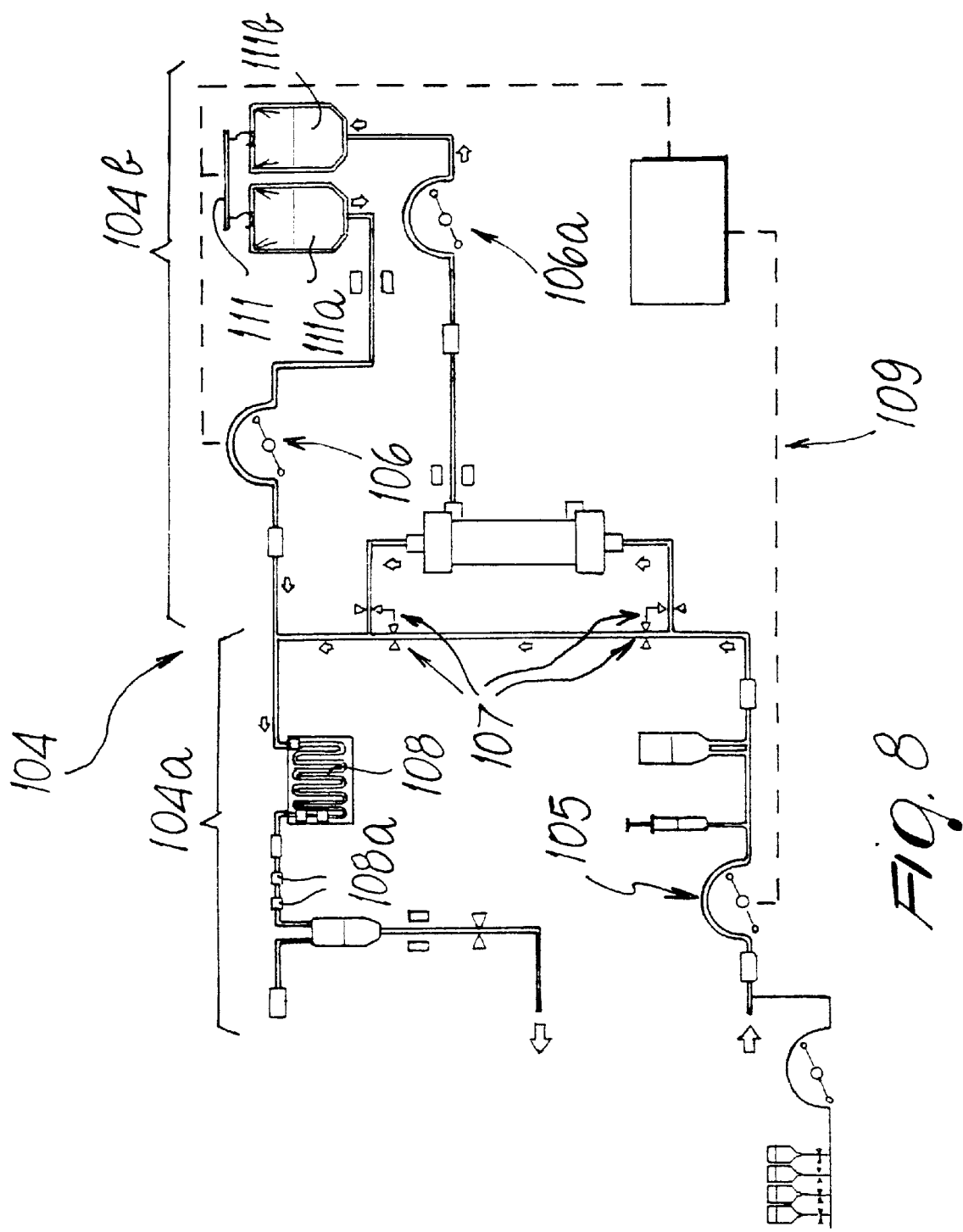
FIG. 8 is a schematic view, similar to FIG. 1, of a more complete version provided with an electronic emergency circuit.

In a second more complete version, shown in the diagrams of FIGS. 7 and 8, the multipurpose machine is provided with adsorbent and/or filtering means and with means for controlling and regulating chemotherapy and chemofiltration; these means are arranged along a first set of duct circuits 104 accommodated inside the head 2 and divided into at least two main loops 104a and 104b, each of which is provided with its own pumping means, designated, respectively, by 105, 106 and 106a which mutually interact or can be separated thanks to the intervention of clamp means 107.

A first loop 104a of the loops is meant for the infusion of chemotherapeutic agents and is provided with a heating means 108, whereas a second loop 104b is meant for the filtration of the chemotherapeutic agents, as in the already described embodiment.

An electronic emergency circuit, generally designated by 109, is inserted between the two main loops 104a and 104b and is meant for the detection of malfunctions of the pumping means 105 and 106 and for the consequent functional restoration of at least the infusion loop 104a.

The emergency electronic circuit 109 is connected to each one of the pumping means 105 and 106 of the main loops 104a and 104b and to a weighing element 111 which is meant to control the exchange volumes during the filtration of the chemotherapeutic agents extracted from the patient.

The head 2 further accommodates a second main set of circuits 110 which can be alternately activated with respect to the first set of circuits 104 in order to perform intraperitoneal hyperthermal perfusion therapy.

The second main set of circuits 110 comprises a closed loop 110a which leads into the peritoneal region of the patient, schematically designated by 112, and a branch loop 110b for feeding the chemotherapeutic agents; accordingly, along this loop there is a means 114 for containing and weighing the chemotherapeutic agents; on the same closed loop 110a there are also, in a series arrangement, a heating means 115 and a pumping means 116, upstream and downstream of which there are infusion pressure sensors, designated by 117 and 118 respectively.

Sensors 113 for detecting the temperature of the infused substances are also inserted in the peritoneal region 112 of the patient and are adapted to control, by averaging it, the value of the temperatures detected locally.

In the branch loop 110b, the inlet 120 and the outlet 119 are respectively located upstream and downstream of the series of dispensers/sensors 113 and their access is regulated by corresponding clamp means 122a and 122b which control the connection of the chemotherapeutic agent container and weighing means 114.

In the preferred and advantageous embodiment of the invention, both the pumping means 116 and the heating means 115 can also be mutually used in the main loops 104a and 104b and coincide with the corresponding means 106 and 108.

The pumping means 105, 106, 106a and 116 are all constituted by pumps of the peristaltic type and the means 114 for containing and weighing the exchange volumes is constituted by a pouch 123, or an ampoule supported by a load cell, schematically designated by 123a; the same applies to the weighing element 111, which is provided with two bags 111a and 111b.

The heating means 115 or 108 is provided with a set of three sensors 124 for detecting the invasive temperature.

The operation of the invention is described hereinafter by referring separately to the two possible embodiments of the multipurpose machine according to the invention; for the first, simpler embodiment, this operation is as follows: the machine 1 is preset in the operating configuration, as shown in FIGS. 4 and 6.

The screen 11 is removed from its seat 11a and the adsorbent and/or filtering means 6 are placed in the appropriate recesses 10a of the plate 10, connected to the set of circuits 12.

The ends of the set of duct circuits 12 are connected to the patient and the medical operator sets on the screen 11, by touching in each instance the surface thereof at the different displayed parameters, the preset values of these parameters in order to correctly perform the chemotherapy session.

In practice, as soon as the therapeutic cycle begins, the machine 1 draws the blood from the patient, feeds into the extracorporeal circuit 12 and then returns it to the patient.

The first sensor means 16 controls the withdrawal pressure of the blood drawn by the peristaltic pump 18.

In a first step of the administration of the chemotherapeutic agents, designated by C in the drawings, the valve means 20 and 30 are arranged so as to temporarily cut off the second loop 12b.

The chemotherapeutic agents C are fed into the first loop 12a of the circuit 12 in the point 17, and their outflow speed and their sequence and volume of administration are determined by the operator, who sets them on the screen 11.

The second sensor means 19 controls the correctness of the pressure values of the chemotherapeutic agents inside the loop 12a and at the inlet in the loop 12b.

The blood of the patient then flows through the intermediate segment 14 of the loop, passing through the sensor 21, which systematically detects the pressure values of the oxygen contained therein.

The sensor 21 can, for particular applications, assume the structure of a sound or probe which can be arranged directly in contact with the tissues of the organ that is the target of the chemotherapeutic agents; the organ is isolated beforehand from the rest of the body according to conventional techniques, so as to be able to concentrate thereon the action of the chemotherapeutic agents.

Downstream of the sensor 21 there is the heating means 22 which, in the presence of medicines whose therapeutic action increases as a function of temperature, raises the temperature to bring the blood to the optimum values required by the medicines.

Downstream of the heating means 22 there is the third sensor means 23, detecting and controlling the pressure of the blood returned to the patient, by passing through the third branch or segment 15, along which the fourth sensor 24 checks for any presence of air: if air is present, the fourth sensor means blocks the action of the peristaltic pump 18 before the air reaches the patient.

The electric clamp 25 prevents, in the general operating condition, the accidental infusion of air to the patient if the presence of air is detected by the sensor means 24; moreover, when the pump 18 is not moving, it does not allow the reverse flow of the blood from the patient.

When the sensor 21 detects a drop in the oxygen pressure in the blood below a preset value, it actuates the change of the opening of the valve and clamp means 20 and 30 that close the portion 14 and open the path of the second loop 12b, in which the blood is purified of the chemotherapeutic agents.

The blood in fact passes through the adsorbent or filtering means 28 in countercurrent, according to the conventional method of hemofiltration or hemodialysis, with a replacement or dialysis solution whose flow is kept in circulation by the pumping assembly 35.

The fifth sensor means 31 checks for any blood presence in the filtered solution that circulates in the sub-loop 29 arriving from the filtering means 28, and the sixth sensor means 32 checks its pressure values so that they remain within the intended ranges in order to ensure the integrity of the filtering unit 28 (more specifically, of its membrane).

If the sensor means 31 detects the presence of blood in the filtered solution, a signal warns the operators that the filtering means 28 is damaged and must therefore be replaced.

The depleted solution is collected in the weighing station 34, from which a weighed amount of fresh solution is drawn and is fed, by means of the pumping assembly 35, back into the segment 14 of the first loop 12a, adding oxygen and simultaneously therefore diluting the concentration of the blood returned to the patient; simultaneously, the programmable water balance of the patient is maintained, with a retroactive effect, by the weighing station 34, which regulates the flow-rate of the pumping assembly 33 as a function of the flow-rate of the pumping assembly 35.

The electric clamp 30 is kept in the closed configuration when the infusion of the chemotherapeutic agents in the first loop 12a is in progress and is open when the blood washing step is in progress in the second loop 12b.

The above-described operating cycle is repeated at each session automatically: the health operator can, in each instance, modify the different characteristic parameters on the machine 1, adapting them to the specific requirements of each patient.

Moreover, the presence of the sensor 21 allows to switch the steps of chemotherapeutic agent administration and of patient blood filtration in an absolutely automatic way depending on preset values of the pressure of the oxygen that is present in the blood, which can be preset on the machine 1.

In the more complete embodiment of the machine, operation is substantially similar, the only difference being that the medical operator can select on the screen of the machine the type of oncological therapy to be performed, i.e., intraperitoneal hyperthermal chemotherapy, also known by the acronym IPHC, or hypoxic perfusion, known as "stop-flow".

The execution of the latter has been described above, whereas the former is described hereafter with reference to FIGS. 7 and 8.

The presence of the emergency electronic circuit 109 provided on the machine 1 allows the medical operator to be warned if one of the peristaltic pumps 105 or 106 stops accidentally.

The most dangerous situation for the patient occurs when the pump 105 stops, because if this stoppage occurs when the chemotherapeutic agents have already been administered to the patient at their maximum concentration, the stoppage of the pump 105 prevents their subsequent necessary extraction from the infusion region, since the loop 104a is practically deactivated.

For this reason, the alarm generated by the circuit 109 allows the operator to connect the second loop 104b to the first loop 104a and promptly disconnect the duct in input to the pump 105 and connect it to the pump 106 of the second filtration loop 104b, which accordingly replaces it, restoring the functionality of the loop 104a so that the medicines can be extracted from the patient and collected in an appropriately provided pouch 11a suspended from the weighing element 111.

The control of the water balance of the patient is in any case monitored by the machine 1 through the circuit 109 automatically: through this circuit, the machine 1 in fact reads the values supplied by the weighing element 111, and if necessary it resorts to the administration of a balancing physiological solution drawn from the corresponding dispensing pouch 111a; the administration occurs simply by gravity and therefore without the intervention of the pump 106 normally provided for this purpose.

If the health operator chooses intraperitoneal hyperthermal chemotherapy, in the machine 1 the second main set of circuits 110 is activated and the first set of circuits 104 is bypassed.

In practice, the administration of the solution that contains the chemotherapeutic agents again occurs under the constantly monitored control of the machine 1: this solution arrives from the pouch or ampoule 123 suspended from the corresponding load cell 123a, when the branch loop 110b is directly connected to the pump 116, which sends it into the peritoneum 112 of the patient through the loop 110a.

The heating means 115, provided with the set of three heat sensors 124 and with the signal arriving from the sensors 113, maintains the solution that contains the chemotherapeutic agents at a constant infusion temperature, which can be set to a preset value; the pressure sensors 117 and 118 also keep the infusion pressure under control.

When the latter is completed, by acting on the clamp means 122a and 122b the loop 110b is circuitally bypassed; the solution is recirculated for a preset time interval and subsequently extracted from the peritoneum of the patient, acting again on the clamps 122a and 122b.

In practice it has been observed that the above-described invention achieves the intended aim and object.

The invention thus conceived is susceptible of numerous modifications and variations, all of which are within the scope of the inventive concept.

All the details may further be replaced with other technically equivalent ones.

In practice, the materials employed, as well as the shapes and the dimensions, may be any according to requirements without thereby abandoning the scope of the protection of the appended claims.

The disclosures in Italian Patent Application No. MO99A000259 from which this application claims priority are incorporated herein by reference.

What is claimed is:

1. A multipurpose machine for monitoring and control of locoregional therapies in oncology, comprising:

a head having a box-like structure;

a base for supporting said head;

dimension adjustment means for modifying overall dimensions of the machine;

adsorbent/filtering means, accommodated within said head, for chemofiltration;

perfusion chemotherapy and chemofiltration controlling and regulating means accommodated within said head for controlling and regulating chemotherapy and chemofiltration;

at least one set of duct circuits accommodated within said head and forming at least first and second loops defining, respectively, first and second extracorporeal blood circuits, said first and second loops being connected to each other so as to selectively enable fluid circulation in a separate perfusion configuration for chemotherapy fluid perfusion along the first extracorporeal blood circuit and an interactive chemofiltration configuration for fluid chemofiltration along the second extracorporeal blood circuit, said adsorbent/filtering means and said perfusion chemotherapy and chemofiltration controlling and regulating means being arranged along said at least one set of duct circuits;

and wherein said perfusion chemotherapy and chemofiltration controlling and regulating means includes fluid flow control valve means for interrupting fluid circulation between said first and second loops in said separate perfusion configuration and for enabling fluid flow circulation between said first and second loops in said interactive chemofiltration configuration.

2. The multipurpose machine of claim 1, comprising a second set of duct circuits, accommodated within said head, said second set of duct circuits activated alternatively with respect to said first set of duct circuits in order to perform intraperitoneal hyperthermal perfusion therapy.

3. The multipurpose machine of claim 2, wherein said second set of duct circuits is provided with a closed loop, with a series of dispensers/detection sensors, to which said closed loop leads, which can be introduced in a peritoneal region of a patient, with a branch loop for feeding solution containing chemotherapeutic agents, with a weighing means for containing and weighing the solution, fitted along said branch loop, with a heating means, with a pumping means, said heating and pumping means being further provided in series on said closed loop, and with infusion and circulation pressure sensing means being arranged upstream and, respectively, downstream of said heating and pumping means.

4. The multipurpose machine of claim 3, wherein said second set of duct circuits comprises respective inlet and outlet ends of said branch loop arranged upstream and downstream of said series of dispensers/sensors, and corresponding clamp means, located on said inlet and outlet ends, which control connection to said weighing means.

5. The multipurpose machine of claim 3, wherein said pumping means and said heating means are provided so as to be selectively connectable for operation with both said second main loop and said second set of duct circuits.

6. The multipurpose machine of claim 3, wherein said weighing means include a pouch/ampoule supported by a load cell.

7. The multipurpose machine of claim 2, wherein said first loop includes at least three mutually sequential duct segments: a first segment for drawing blood from a patient and for introducing the chemotherapeutic agents; a second intermediate segment for blood control; and a third segment for returning the blood to the patient.

8. The multipurpose machine of claim 7, further comprising: pumping means, arranged at said first and second loop, for pumping fluid in said set of duct circuits forming said first and second loops; and an electronic emergency circuit which is inserted between said two selectively interactive and separate configuration first and second loops, for managing malfunctions of said pumping means whereupon functionally restoring operation of at least said first infusion loop.

9. The multipurpose machine of claim 8, wherein said emergency electronic circuit is connected to said pumping means of said first and second loops and to said adsorbent/filtering means for filtering the chemotherapeutic agents.

10. The multipurpose machine of claim 9, wherein said electronic circuit is connected to said pumping means so as to carry out, upon malfunction of said first loop, active functional switching between the pumping means of said second and first loops.

11. The multipurpose machine of claim 11, wherein said chemotherapy and chemofiltration controlling and regulating means further include, arranged in a cascade arrangement along said first segment: a first blood pressure sensor means for sensing blood pressure at withdrawal from a patient which is connected to a point of said first segment for introducing the chemotherapeutic agents; a pumping assembly arranged downstream of said point of the first segment; and a second sensor means for controlling inlet pressure of the chemotherapeutic agents.

12. The multipurpose machine of claim 11, wherein said pumping assembly includes a pump of a peristaltic type.

13. The multipurpose machine of claim 11, wherein said perfusion chemotherapy and chemofiltration controlling and regulating means further includes, arranged in a series arrangement along said second intermediate segment: an oxygen pressure sensing means for sensing pressure of the oxygen in the blood in said first loop; a heating means, provided downstream of said oxygen pressure sensing means; and a third blood pressure sensor means for measuring the pressure of the blood returning to the patient, said fluid flow control valve means including a first throttling/connection valve means for throttling and respectively enabling fluid flow between said first and second loops.

14. The multipurpose machine of claim 13, wherein said perfusion chemotherapy and chemofiltration controlling and regulating means further includes, arranged in a series arrangement along said third segment for blood return: a fourth air sensor means for detecting air in the blood returned to the patient; and at least one terminal electric clamp to prevent reverse flow of the blood.

15. The multipurpose machine of claim 14, wherein said perfusion chemotherapy and chemofiltration controlling and regulating means further include: a multiple-way valve means provided so as to control, both sequentially and with time-dependent criteria, fluid flow at said point for introducing the chemotherapeutic agent.

16. The multipurpose machine of claim 14, wherein said pumping assembly is controlled by said first blood pressure sensing means and by said third blood pressure sensor means.

17. The multipurpose machine of claim 16, wherein said fluid flow control valve means is provided so as to be controlled by said oxygen pressure sensing means.

18. The multipurpose machine of claim 17, wherein said oxygen pressure sensing means includes a probe adapted to be placed in direct contact with an organ which is target of the chemotherapeutic agents.

19. The multipurpose machine of claim 14, wherein said electric clamp is provided so as to be controlled by said fourth air sensor means for detecting air in blood being returned to the patient.

20. The multipurpose machine of claim 14, wherein said second chemotherapeutic agent filtration loop includes two sub-loops: a first sub-loop including the adsorbent/filtering means for filtering the chemotherapeutic agents; and a second sub-loop for controlling functionality of said adsorbent/filtering means and for maintaining a presettable water balance of the patient.

21. The multipurpose machine of claim 20, wherein said perfusion chemotherapy and chemofiltration controlling and regulating means further include: at least one further electric clamp, said first sub-loop being connectable to said intermediate segment of said first loop, in input, through said fluid flow control valve means, and in output, directly upstream of said oxygen sensing means, through said at least one further electric clamp for throttling said connection in output.

22. The multipurpose machine of claim 21, wherein said second sub-loop includes a conventional set of circuits for hemofiltration and hemodialysis.

23. The multipurpose machine of claim 22, further comprising: at least one fifth blood sensor means provided at said second sub-loop for detecting presence of blood in said second sub-loop; a sixth pressure sensing means serially connected to said fifth blood sensor means for sensing pressure in output from said filtering means; a second pumping assembly located downstream of said sixth pressure sensing means; a weighing station provided downstream of said pumping assembly; a third pumping assembly arranged downstream of said weighing station; and a seventh sensing means for sensing and controlling pressure in said second sub-loop.

24. The multipurpose machine of claim 1, wherein said dimension-modifying adjustment means include a trolley which is integrated in said head, by a vertical post on which said trolley is slidingly guided, and by a base from which said post rises.

25. The multipurpose machine of claim 1, further comprising supporting elements, provided at said head for supporting said adsorbent/filtering means and said perfusion chemotherapy and chemofiltration controlling and regulating means, which include at least one plate which is retractably foldable into said head, said plate being provided with corresponding recesses for accommodating said adsorbent/filtering means and said perfusion chemotherapy and chemofiltration controlling and regulating means.

26. The multipurpose machine of claim 25, wherein said perfusion chemotherapy and chemofiltration controlling and regulating means further include: a controller which is provided with a touch-screen, said touch-screen being foldable onto said head into a fold-away position.

\* \* \* \* \*